(12) United States Patent
Wiley et al.

(10) Patent No.: US 12,408,957 B2
(45) Date of Patent: Sep. 9, 2025

(54) ORTHOPAEDIC IMPLANT SYSTEM FOR COMPRESSION-DISTRACTION OF JOINTS

(71) Applicant: Pace Surgical, Inc., Malvern, PA (US)

(72) Inventors: Roy C. Wiley, North Webster, IN (US); Lew C. Schon, Baltimore, MD (US); Malik S. Siddique, Newcastle upon Tyne (GB)

(73) Assignee: Pace Surgical, Inc., Malvern, PA (US)

( * ) Notice: Subject to any disclaimer, the term of this patent is extended or adjusted under 35 U.S.C. 154(b) by 312 days.

(21) Appl. No.: 17/945,944

(22) Filed: Sep. 15, 2022

(65) Prior Publication Data

US 2023/0088758 A1 Mar. 23, 2023

Related U.S. Application Data

(60) Provisional application No. 63/246,552, filed on Sep. 21, 2021.

(51) Int. Cl.
| | |
|---|---|
| *A61B 17/80* | (2006.01) |
| *A61B 17/02* | (2006.01) |
| *A61B 17/66* | (2006.01) |
| *A61B 17/68* | (2006.01) |
| *A61B 17/72* | (2006.01) |

(Continued)

(52) U.S. Cl.
CPC ........ *A61B 17/8004* (2013.01); *A61B 17/025* (2013.01); *A61B 17/66* (2013.01); *A61B 17/68* (2013.01); *A61B 17/686* (2013.01); *A61B 17/7216* (2013.01); *A61B 17/7225* (2013.01); *A61B 17/8014* (2013.01); *A61B 17/8061* (2013.01); *A61F 2002/30622* (2013.01); *A61F 2/4225* (2013.01); *A61F 2002/4228* (2013.01); *A61F 2002/4233* (2013.01); *A61F 2002/4238* (2013.01); *A61F 2/4241* (2013.01);

(Continued)

(58) Field of Classification Search
CPC . A61B 17/8004; A61B 17/80; A61B 17/8014; A61B 17/8061; A61B 17/808; A61B 17/66; A61B 17/68; A61B 17/025; A61B 17/7216; A61B 17/7225; A61B 17/686; A61B 2017/681; A61F 2/42; A61F 2/4225; A61F 2/4241; A61F 2/4261; A61F 2002/4228; A61F 2002/4233; A61F 2002/4238; A61F 2002/4243; A61F 2002/4251; A61F 2002/30622
USPC ........ 606/282, 86 R, 87, 90, 105, 86 B, 902, 606/906, 915, 280, 70, 281, 286, 298, 606/300

See application file for complete search history.

(56) References Cited

U.S. PATENT DOCUMENTS

| | | | |
|---|---|---|---|
| 2008/0177263 A1* | 7/2008 | Freedman | A61B 17/7059 606/71 |
| 2009/0076555 A1* | 3/2009 | Lowry | A61B 17/70 606/280 |
| 2018/0028242 A1* | 2/2018 | Parekh | A61B 17/8061 |

* cited by examiner

*Primary Examiner* — Marcela I. Shirsat
(74) *Attorney, Agent, or Firm* — Knobbe Martens Olson & Bear, LLP (57) ABSTRACT

An orthopaedic implant system includes an orthopaedic implant having a plurality of fixation openings and a plug opening defining a plug opening diameter that is greater than a diameter of any of the fixation openings. The plurality of fixation openings include at least one first fixation opening configured to accept a fixation element inserted in a first bone and at least one second fixation opening configured to accept a fixation element inserted in a second bone. The plug opening is configured to accept a plug inserted in a joint (Continued)

space between the first bone and the second bone to cause compression distraction of the first bone and the second bone.

23 Claims, 7 Drawing Sheets

(51) Int. Cl.
*A61F 2/30* (2006.01)
*A61F 2/42* (2006.01)
(52) U.S. Cl.
CPC .................. *A61F 2002/4243* (2013.01); *A61F 2002/4251* (2013.01); *A61F 2/4261* (2013.01)

ORTHOPAEDIC IMPLANT SYSTEM FOR COMPRESSION-DISTRACTION OF JOINTS

CROSS REFERENCE TO RELATED APPLICATIONS

This is a non-provisional application based upon U.S. provisional patent application Ser. No. 63/246,552, entitled "ORTHOPAEDIC IMPLANT SYSTEM FOR COMPRESSION-DISTRACTION OF JOINTS", filed Sep. 21, 2021, which is incorporated herein by reference.

BACKGROUND OF THE INVENTION

1. Field of the Invention

The present invention relates to medical implants, and, more particularly, to orthopaedic implants.

2. Description of the Related Art

Many types of orthopaedic surgeries and associated implants are known. One type of known orthopaedic surgery is a fusion surgery, in which two or more bones are fused together using an orthopaedic implant, such as a plate. When a plate is used to perform a fusion, the plate must cross over the natural joint space between the two or more bones.

There are several issues that can detrimentally affect the success of a fusion surgery. In some instances, the fusion site may be prepared in a manner that excessively shortens the overall length of the involved bones, which can lead to unnatural biomechanics at the fusion site. It is also possible that fusion between the bones may not occur due to a lack of compression at the fusion site.

What is needed in the art is a way to address some of the issues with known fusion surgeries and associated orthopaedic implants.

SUMMARY OF THE INVENTION

The present invention provides an orthopaedic implant system including an orthopaedic implant with a plug opening formed therein that is a largest opening of the orthopaedic implant and is sized and configured to accept a plug that can cause distraction of bones and compression of a graft against bone ends when inserted between bones.

In some exemplary embodiments provided according to the present invention, an orthopaedic implant system includes an orthopaedic implant having a plurality of fixation openings and a plug opening defining a plug opening diameter that is greater than a diameter of any of the fixation openings. The plurality of fixation openings include at least one first fixation opening configured to accept a fixation element inserted in a first bone and at least one second fixation opening configured to accept a fixation element inserted in a second bone. The plug opening is configured to accept a plug inserted in a joint space between the first bone and the second bone to cause compression distraction of the first bone and the second bone.

In some exemplary embodiments provided according to the present invention, a method of implanting an orthopaedic implant is provided. The method includes: positioning the orthopaedic implant so at least one first fixation opening of the orthopaedic implant is aligned with a first bone and at least one second fixation opening of the orthopaedic implant is aligned with a second bone; inserting a first fixation element into the first bone through the at least one first fixation opening; and inserting a second fixation element into the second bone through the at least one second fixation opening. A plug opening of the orthopaedic implant is aligned with a joint space between the first bone and the second bone after inserting the first fixation element into the first bone and after inserting the second fixation element into the second bone. The plug opening defines a plug opening diameter that is greater than a diameter of any of the fixation openings and is configured to accept a plug inserted in the joint space to cause compression distraction of the first bone and the second bone.

A possible advantage that may be realized by exemplary embodiments provided according to the present invention is that the plug opening can accept a plug that compresses a graft and/or the bones at the fusion site to maintain the length integrity of the anatomical structures.

Another possible advantage that may be realized by exemplary embodiments provided according to the present invention is that the plug can provide compression across the joint line to support fusion and help keep the joint in a distracted position.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Referring now to the drawings, and more particularly to FIGS. 1-4, there is shown an exemplary embodiment of an orthopaedic implant system 300 (first illustrated in FIG. 3) which generally includes an orthopaedic implant 100 (first illustrated in FIG. 1) and, in some embodiments, a plug 200 (first illustrated in FIG. 2) that is coupled to the orthopaedic implant 100. The orthopaedic implant 100 is shaped and sized to be used for fusing the cuneiform to the first metatarsal, but it should be appreciated that the shape and dimensions of the orthopaedic implant 100 can be adjusted for use in other joint areas, as will be appreciated further herein. The orthopaedic implant 100 includes a plurality of fixation openings 101 formed therein that can accept a fixation element, such as a bone screw, to fixate the orthopaedic implant 100 to the bones of the joint. At least one of the fixation openings 101 may be referred to as a first fixation opening that is configured to accept a fixation element inserted in a first bone and at least one of the other fixation openings 101 may be referred to as a second fixation opening that is configured to accept a fixation element inserted in a second bone, as will be described further herein. The fixation elements may be variable angle or fixed angle fixation elements, which are both known in the art. The orthopaedic implant 100 may be formed of any suitable biocompatible material, including but not limited to: metals such as titanium, cobalt-chrome, stainless steel, and/or alloys thereof; or polymers such as ultra-high molecular weight polyethylene (UHMWPE), polyarylether ketones (PAEK) such as polyether ether ketone (PEEK), and/or blends thereof. The biocompatible material may be partially resorbable, fully resorbable, or minimally resorbable (less than 5% resorption within one year of implantation).

Figure 1:
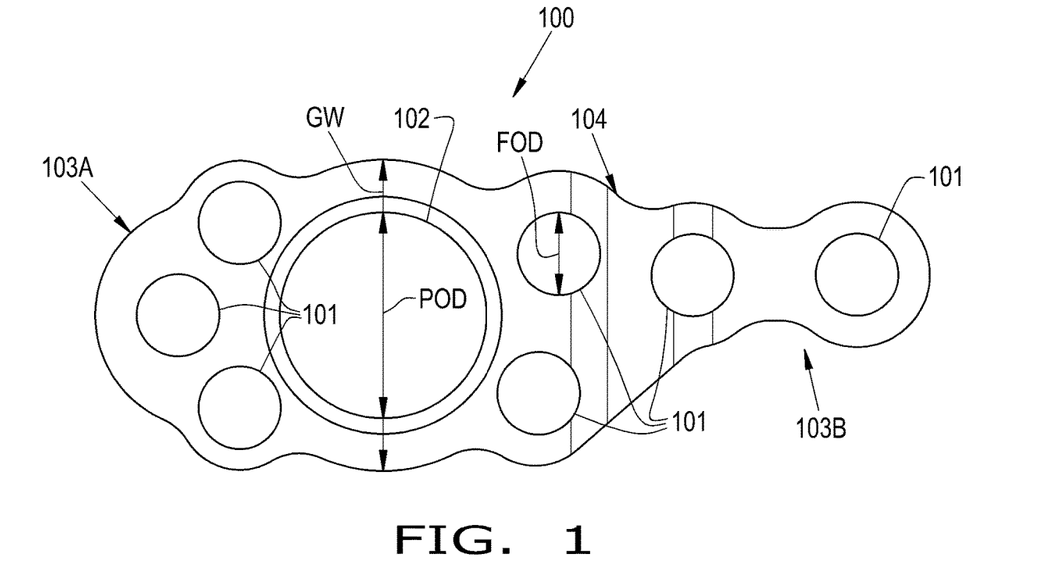
FIG. 1 is a top view of an exemplary embodiment of an orthopaedic implant provided according to the present invention.

The orthopaedic implant 100 also includes a single plug opening 102 that is a largest opening of the orthopaedic implant 100. The plug opening 102 may, for example, define a plug opening diameter POD that is a relatively high percentage of a greatest width GW of the orthopaedic implant 100, e.g., the plug opening diameter POD may be greater than 50% of the greatest width GW, such as 50-90% of the greatest width GW. In addition, or alternatively, the plug opening 102 may define a plug opening diameter POD that is several times a fixation opening diameter FOD of the fixation openings 101. For example, the plug opening diameter POD may be at least double the fixation opening diameter FOD or even at least triple the fixation opening diameter FOD. In other words, the plug opening diameter POD is greater than the fixation opening diameter FOD of any of the fixation openings 101. While the openings 101, 102 are illustrated as being circular, in some embodiments the openings 101, 102 are non-circular or even non-round; in such embodiments, the plug opening diameter POD may correspond to a plug opening width that is a largest dimension of the plug opening 102. Further, it should be appreciated that while the orthopaedic implant 100 is illustrated with a single plug opening 102, in some embodiments the orthopaedic implant 100 includes multiple plug openings, e.g., if the orthopaedic implant spans across more than two bones such as a first bone, a second bone, and a third bone, that are considerably larger than any other openings of the orthopaedic implant 100. In embodiments with multiple plug openings, the diameter of each plug opening may be less than 50% of the greatest width of the orthopaedic implant if necessary, e.g., to prevent the plug openings from overlapping and/or splitting the orthopaedic implant in half.

Figure 4:
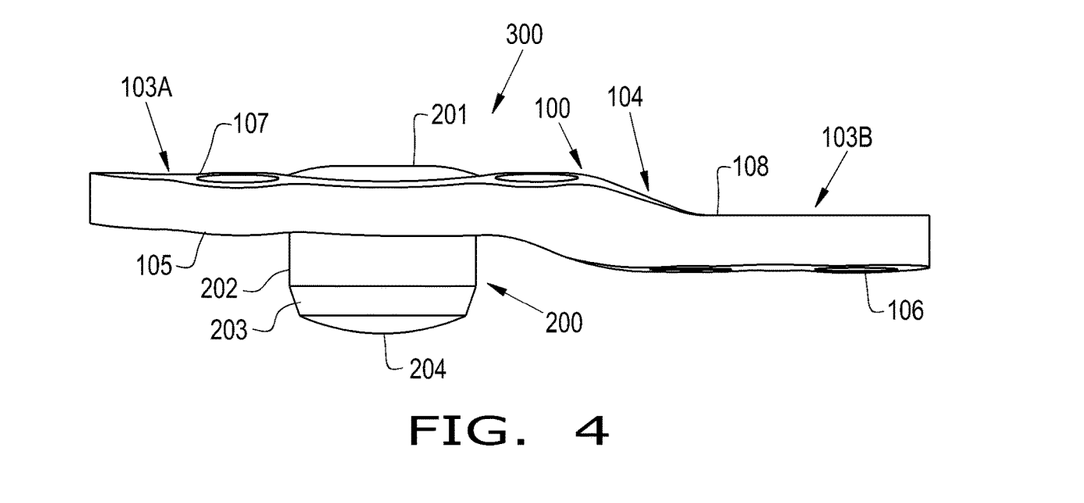
FIG. 4 is a side view of the orthopaedic implant system of FIG. 3.

As best illustrated in FIG. 4, the orthopaedic implant 100 may have two regions 103A, 103B where the openings 101, 102 are formed that are connected by an offsetting region 104 so the regions 103A, 103B are offset from one another. As can be appreciated from FIG. 4, one of the regions 103A, which may be referred to as a second region including the at least one second fixation opening 101, may have a bottom surface 105 that is above a corresponding bottom surface 106 of the other region 103B, which may be referred to as a first region including the at least one first fixation opening 101. In this respect, the bottom surface 106 may represent the bottom surface 106 of the orthopaedic implant 100. Similarly, the second region 103A may have a top surface 107 that is above a corresponding top surface 108 of the first region 103B, with the top surface 107 representing the top surface 107 of the orthopaedic implant 100.

Figure 2:
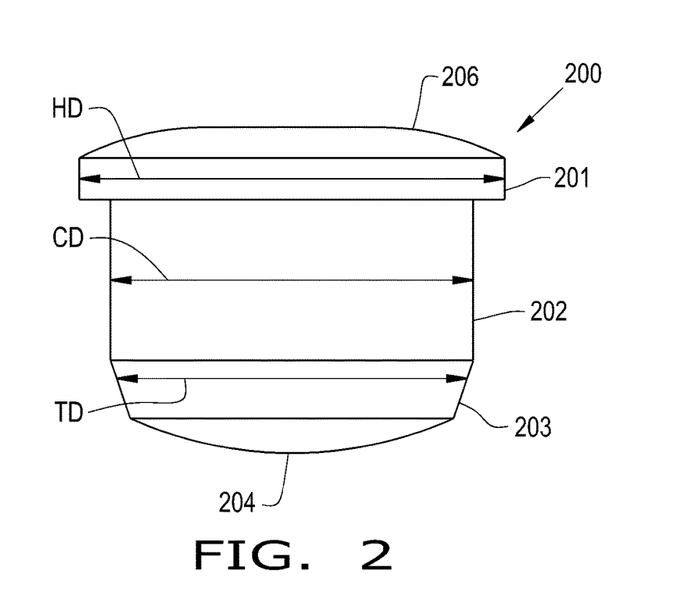
FIG. 2 is a side view of an exemplary embodiment of a plug provided according to the present invention.

Referring specifically now to FIG. 2, the plug 200 that is coupled to the orthopaedic implant 100 to form the orthopaedic implant system 300 is illustrated in greater detail and separate from the orthopaedic implant 100 to better illustrate the features of the plug 200. The plug 200 may include a head 201, a cylindrical section 202 connected to the head 201, and a tapered section 203 connected to the cylindrical section 202. The head 201 may define a head diameter HD that is greater than the plug opening diameter POD to prevent the plug 200 from going through the plug opening 102 when inserted therein, while the cylindrical section 202 and the tapered section 203 may both define respective diameters CD, TD that are less than the plug opening diameter POD. As can be appreciated from FIG. 2, the tapered diameter TD decreases in a direction from the cylindrical section 202 toward a bottom 204 of the plug 200. It should be appreciated that, in some embodiments, the portion of the plug 200 referred to herein as the "cylindrical section" 202 may be tapered, in addition to or alternatively to the tapered section 203. Further, in some embodiments the plug 200 does not include a tapered section. The plug 200 may also include a driver feature 205, illustrated as a driver opening, formed in a top 206 of the plug 200 that is configured to interact with a driver, such as a hex wrench, to drive the plug 200 into the plug opening 102, as will be described further herein. The plug 200 may be partially or completely unthreaded or, in some embodiments, partially or completely threaded. In some embodiments, the plug 200 is formed from a polymer.

Figure 3:
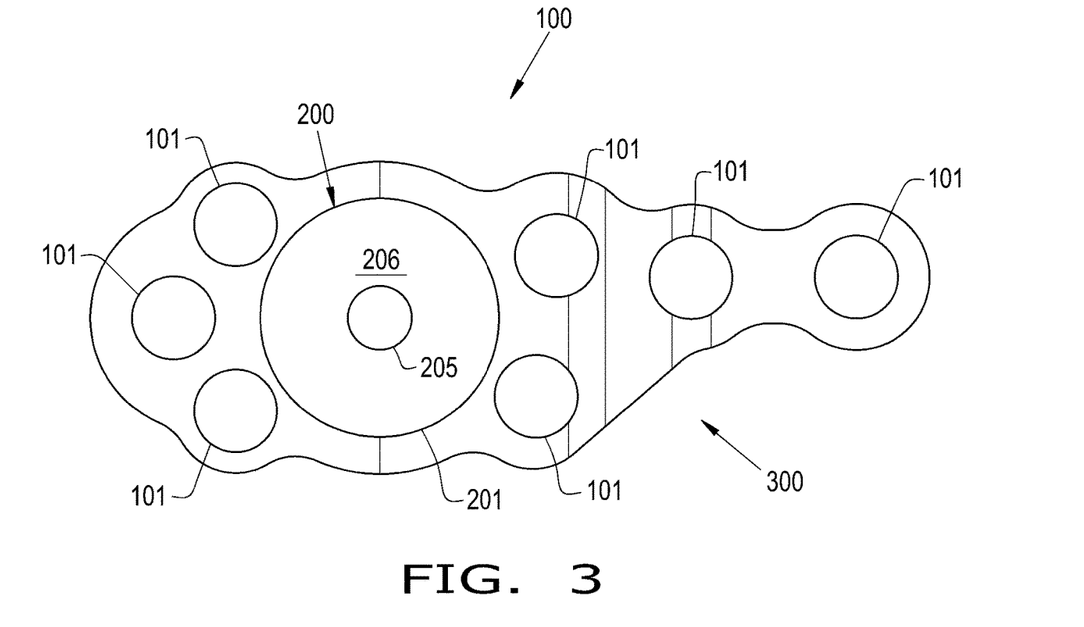
FIG. 3 is a top view of an exemplary embodiment of an orthopaedic implant system including the orthopaedic implant of FIG. 1 as well as the plug of FIG. 2 inserted in a plug opening of the orthopaedic implant.

The plug opening 102 is configured to accept the plug 200 inserted in a joint space between a first bone and a second bone to cause compression distraction of the first bone and the second bone. As illustrated in FIGS. 3-4, the orthopaedic implant system 300 may be formed by inserting the plug 200 in the plug opening 102 of the orthopaedic implant 100. The plug 200 may be inserted until the head 201 of the plug 200 abuts against the top surface 107 of the region 103A, at which point the bottom 204 of the plug 200 is below the bottom surfaces 105, 106 of both of the regions 103A, 103B of the orthopaedic implant 100. In this respect, the plug 200 may extend past the orthopaedic implant 100 into a joint space between two adjacent bones to bear on the bones. When fully inserted, the plug 200 is engaged with the orthopaedic implant 100 so the plug 200 is not easily removed from the orthopaedic implant 100, e.g., by oversizing the plug 200 relative to the plug opening 102 to form an interference fit or by using some other type of engagement such as threads, as will be described further herein.

The plug 200 bearing on the bones may create compression of a graft and/or the graft creates compression against bone ends of the bones while also distracting the bones, leading to compression distraction that can maintain the length integrity of the anatomical structures rather than shortening the length, which is commonly encountered when performing a fusion surgery. In some embodiments, the portion(s) of the plug 200 that extends out of the plug opening 102, when the plug 200 is fully inserted, defines a protruding length of 2-4 mm or 1-7 mm.

Figure 5A:
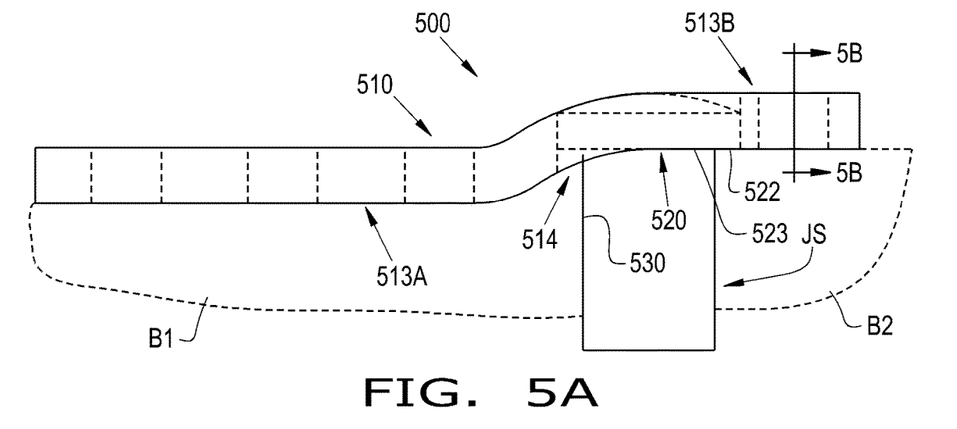
FIG. 5A is a cross-sectional view of an exemplary embodiment of an orthopaedic implant system that is used to fuse a first bone to a second bone including an orthopaedic implant including a plug opening that holds a plug inserted in a joint space between the bones.
Figure 5B:
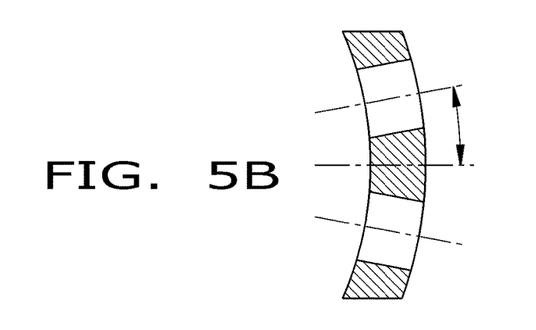
FIG. 5B is a section view taken along line A-A in FIG. 5A.
Figure 5C:
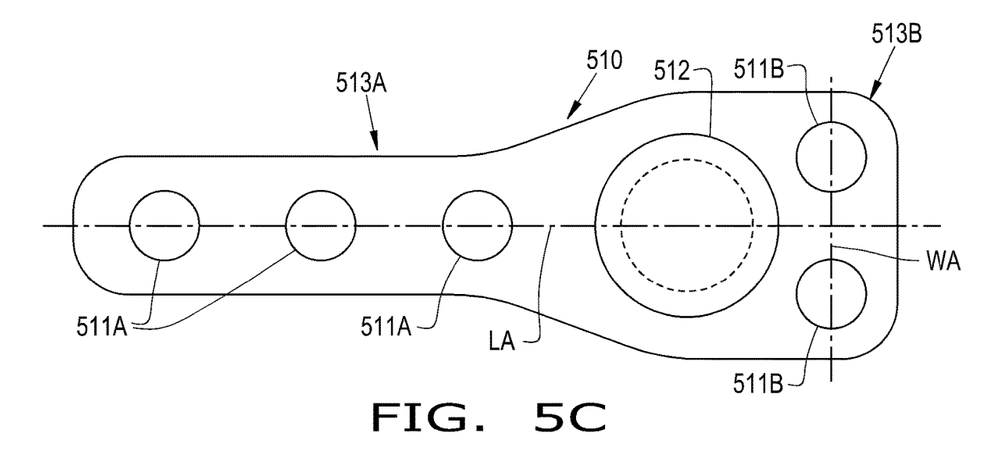
FIG. 5C is a top view of the orthopaedic implant of FIG. 5A.

Referring now to FIGS. 5A-5C, another exemplary embodiment of an orthopaedic implant system 500 is illustrated that includes an orthopaedic implant 510 and a plug 520. The plug 520 may be similar to the previously described plug 200. The orthopaedic implant 510 has a plurality of fixation openings 511A, 511B and a single plug opening 512. The plug 520 is inserted into the plug opening 512. As can be appreciated from FIG. 5C, which illustrates the orthopaedic implant 510 by itself, three of the fixation openings 511A may be aligned with one another so their centers are located along a longitudinal axis LA of the orthopaedic implant 510 while two of the fixation openings 511B may be aligned with one another so their centers are located along a width axis WA of the orthopaedic implant 510. It should be appreciated that the arrangement of the fixation openings 511A, 511B may be adjusted, as desired. The orthopaedic implant 510 includes a first region 513A that includes the fixation openings 511A and a second region 513B that includes the plug opening 512 and the fixation openings 511B. The first region 513A may be connected to the second region 513B by an offsetting region 514 so the first region 513A is lower than the second region 513B. The offsetting region 514 can create a "step" between the first region 513A and the second region 513B, with the step being between, for example, 2-4 mm, depending on the anatomical structures being fused by the orthopaedic implant 510. It should be appreciated that the length and angle of the offsetting region 514 relative to the regions 513A, 513B can adjusted, as desired, to create a step of a desired length, which may be more or less than the previously described 2-4 mm such as 1-8 mm.

As can be seen in FIG. 5A, the first region 513A may be fixated to a first bone B1 by fixation elements extending through the fixation openings 511A, which may also be referred to as first fixation openings. The second region 513B, on the other hand, may be fixated to a second bone B2 by fixation elements extending through the fixation openings 511B, which may also be referred to as second fixation openings. A joint space JS is established between the first bone B1 and the second bone B2. The orthopaedic implant 510 may be placed so the first region 513A is properly placed on the first bone B1 and the second region 513B is properly placed on the second bone B2, with the plug opening 512 being located above, i.e., aligned with, the joint space JS. The regions 513A, 513B may be initially fixed with one or more fixation elements, such as bone screws, inserted in the fixation openings 511A, 511B and into the bones B1, B2. The initial fixation can hold the orthopaedic implant 510 in place during subsequent surgical steps.

A plug of tissue may be harvested from the joint space JS and replaced with a graft 530 that may be greater in size than the harvested plug of tissue. The plug of tissue may be harvested through the plug opening 512 of the orthopaedic implant 510, which may be left open, so the orthopaedic implant 510 does not need to be positioned following plug harvesting. It should thus be appreciated that the harvested plug of tissue may have a diameter (or width) that is smaller than the corresponding diameter (or width) of the plug opening 512. The graft 530 may also be inserted into the joint space JS through the plug opening 512. The graft 530 may be, for example, biological tissue such as an autograft, allograft, etc., a scaffold configured to allow tissue ingrowth, or a combination of both. The graft 530 may have a diameter that is 1-2 mm greater than that of the harvested plug of tissue so the graft 530 can compress against the bones 510, 520. After the graft 530 is placed, additional fixation elements can be inserted into the fixation openings 511A, 511B and the bones B1, B2 to fully secure the orthopaedic implant 510 to the bones B1, B2 and the plug 520 can be inserted into the plug opening 512 to cause compression distraction of the first bone B1 and the second bone B2. In some embodiments, the plug 520 is inserted into the plug opening 512 prior to inserting additional fixation elements into the fixation openings 511A, 511B; in some embodiments, additional fixation elements are inserted into the fixation openings 511A, 511B prior to inserting the plug 520 into the plug opening 512.

The plug 520 extends through the plug opening 512 so a portion of the plug 520 compresses the graft 530, which maintains the graft 530 in place. As the plug 520 is inserted, a tapered section 523 of the plug 520 can gradually create distance between the bones B1, B2 to distract the bones B1, B2. A portion of the plug 520, such as a cylindrical section 522 of the plug 520, can contact cortical bone after the plug 520 is fully inserted in the plug opening 512 to distract the bones B1, B2 and maintain the length integrity of the anatomical structures by not allowing the bones B1, B2 to migrate toward one another. Thus, the plug 520 can create compression between the graft 530 and the bones B1, B2 and distraction on the bones B1, B2 so the anatomical structures do not shorten following the fusion. It should be appreciated that while the procedure of implanting an orthopaedic implant system 500 is described in the context of FIGS. 5A-5C, a similar procedure can be utilized for other orthopaedic implant systems provided according to the present invention, including but not limited to the previously described orthopaedic implant system 300 and orthopaedic implant systems described further herein.

Figure 6A:
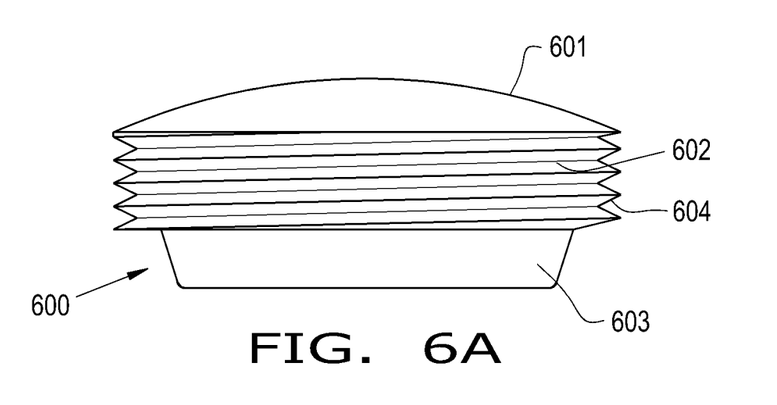
FIG. 6A is a side view of an exemplary embodiment of a plug provided according to the present invention for use in an orthopaedic implant system.
Figure 6B:
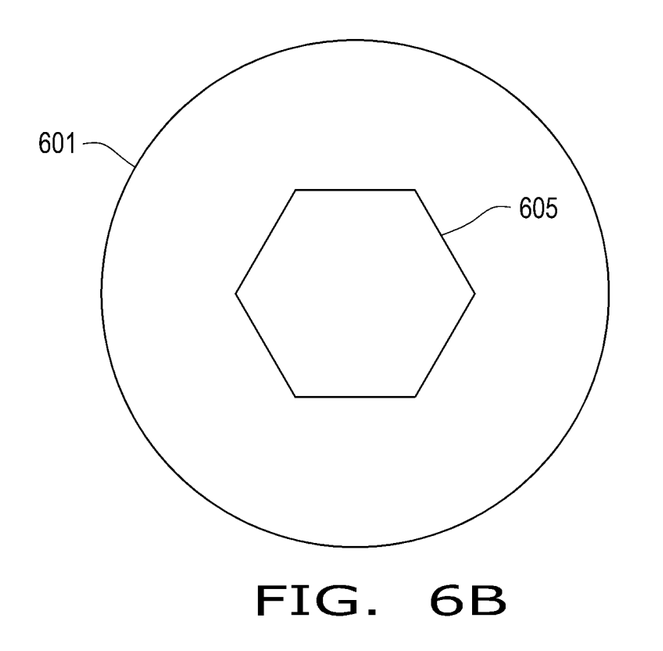
FIG. 6B is a top view of the plug of FIG. 6A.
Figure 6C:
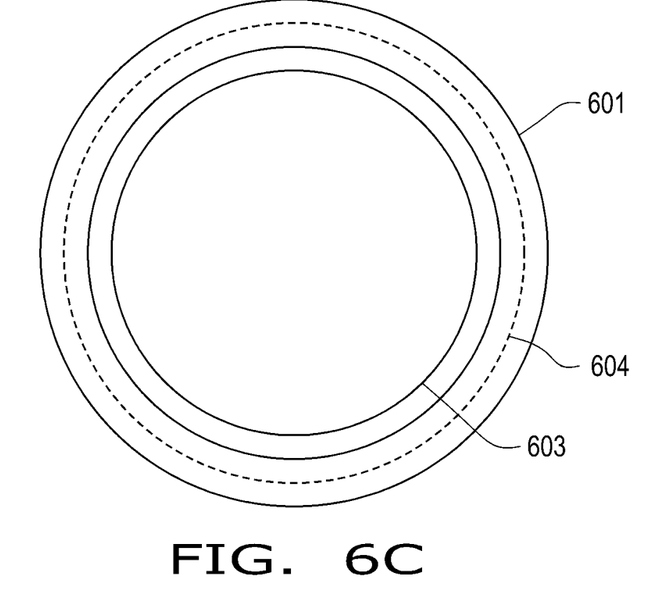
FIG. 6C is a bottom view of the plug of FIGS. 6A and 6B.

Referring now to FIGS. 6A-6C, another exemplary embodiment of a plug 600 that can be used in an orthopaedic implant system is illustrated. The plug 600 may have a similar shape to the previously described plugs 200, 520 and have threads 604 formed on an exterior of the plug 600, such as a cylindrical section 602 of the plug 600. In some embodiments, some of the threads 604 also extend to a head 601 of the plug 600. The plug 600 may also have a tapered section 603 connected to the cylindrical section 602. The plug 600 may further include a driver feature 605, such as a hex-shaped opening, that is configured to accept a driver, such as a hex-head wrench, to drive the plug 600. By threading the plug 600, the plug 600 can be driven into an opening formed in bone tissue that has a smaller diameter than the plug 600, i.e., the plug 600 is oversized relative to the opening formed in the bone tissue. The plug 600 being oversized relative to the opening formed in the bone tissue allows the plug 600 to tightly fit against the bone tissue, such as cortical bone tissue, and help compress a graft against bones ends and distract the bones. The threads 604 can also interact with corresponding threads formed in a plug opening of an orthopaedic implant, in which the plug 600 is inserted, to hold the plug 600 in place following implantation so the plug 600 is not, for example, squeezed out from the plug opening by the bones compressed by the plug 600.

Figure 7:
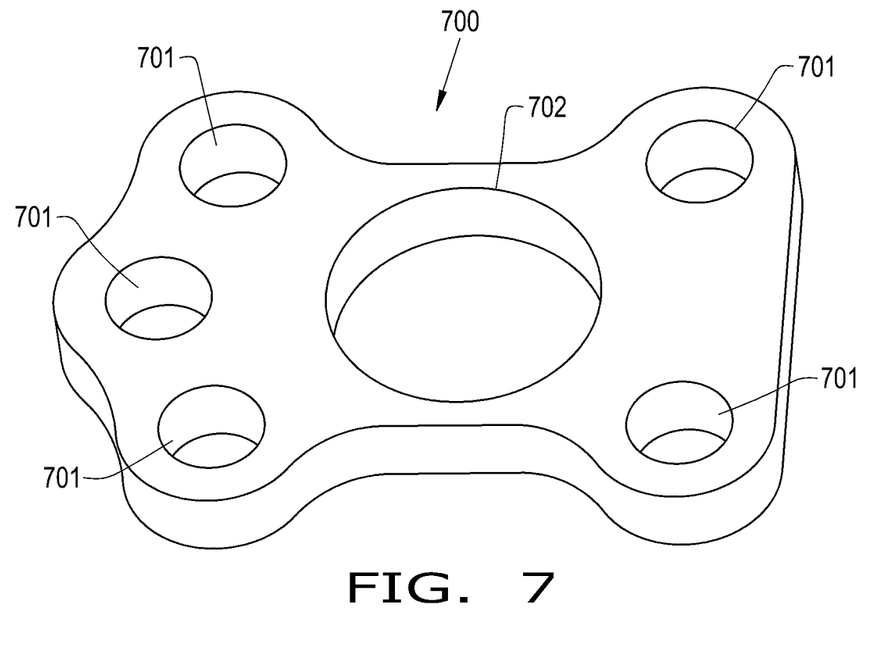
FIG. 7 is a perspective view of another exemplary embodiment of an orthopaedic implant provided according to the present invention.

Referring now to FIG. 7, another exemplary embodiment of an orthopaedic implant 700 that may be used in an orthopaedic implant system with a plug is illustrated. The illustrated shape of the orthopaedic implant 700 may be configured, for example, to perform a talar-navicular fusion. As illustrated, the orthopaedic implant 700 has a plurality of fixation openings 701 and a single plug opening 702 formed therein. The plug opening 702 may be considerably larger than any of the fixation openings 701, as previously described. The plug opening 702 may be placed so it overlaps the geometric center of the orthopaedic implant 700. The fixation openings 701 may be placed around the plug opening 702, as illustrated, to fixate the orthopaedic implant 700 to bones. It should thus be appreciated that the orthopaedic implants provided according to the present invention can be formed with many different general shapes and arrangements of openings depending on the anatomical location where the orthopaedic implant is being used, e.g., at various locations in the foot, hand, etc. It should be further appreciated that the orthopaedic implants provided according to the present invention may be shaped and configured for use to span one joint between two bones or multiple joints, such as two joints, between more than two bones.

Figure 8:
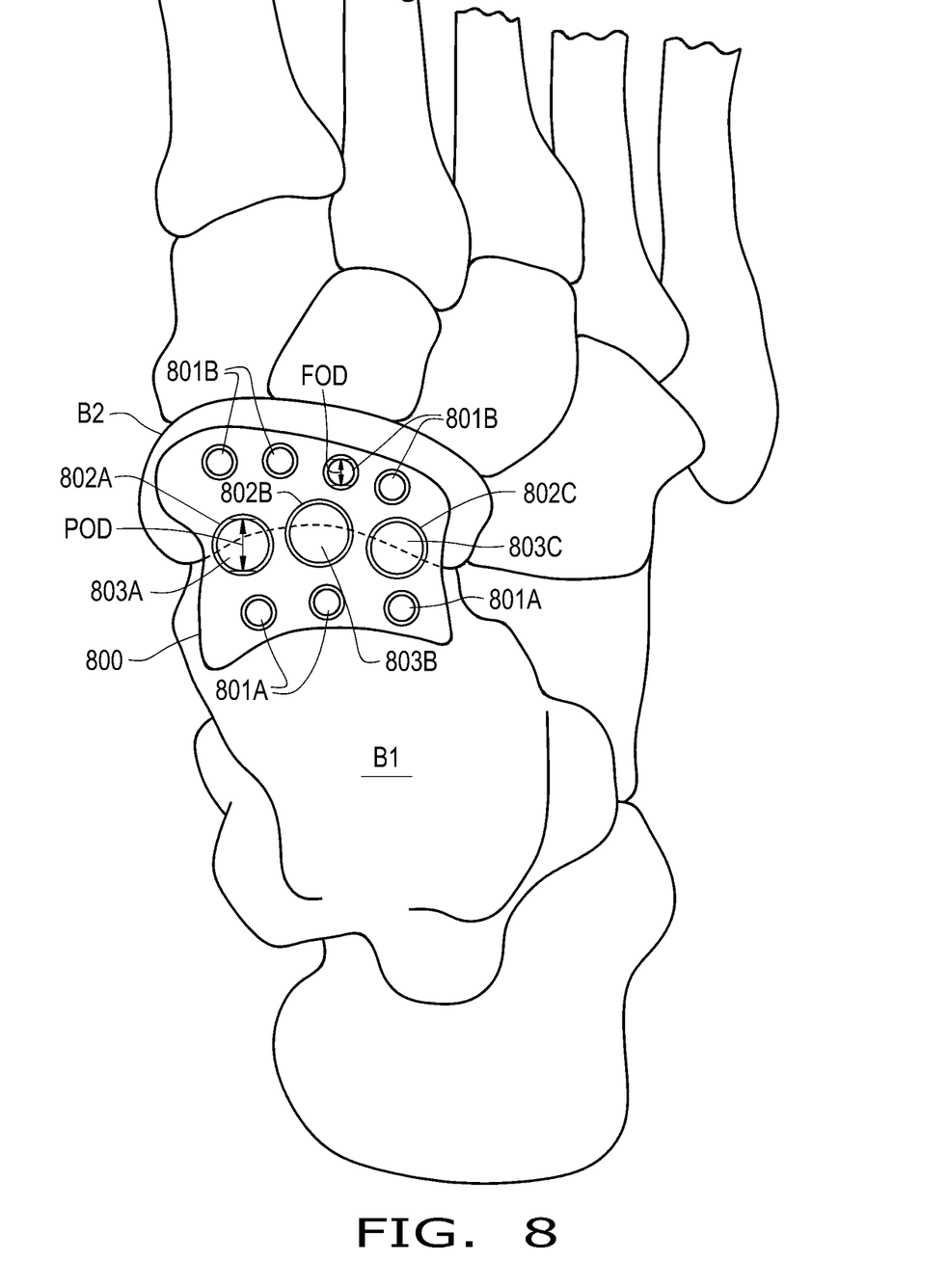
FIG. 8 is a top view of another exemplary embodiment of an orthopaedic implant system provided according to the present invention that includes an orthopaedic implant with multiple plug openings and a plug disposed in each of the plug openings.

As previously described, orthopaedic implants provided according to the present invention may include multiple plug openings that are each configured to accept a respective plug. Referring now to FIG. 8, an exemplary embodiment of an orthopaedic implant system including an orthopaedic implant 800 provided according to the present invention is illustrated that includes a plurality of fixation openings 801A, 801B and a plurality of plug openings 802A, 802B, 802C. The fixation openings 801A, which may be referred to as first fixation openings, are configured to accept a fixation element inserted in a first bone B1, illustrated as a talus, and the fixation openings 801B, which may be referred to as second fixation openings, are configured to accept a fixation element inserted in a second bone B2, illustrated as a navicular. Each of the fixation openings 801A, 801B may define a fixation opening diameter FOD that is the same. The plug openings 802A, 802B, 802C, on the other hand, each define a plug opening diameter POD that is greater than the fixation opening diameter FOD of any of the fixation openings 801A, 801B. Each of the plug openings 802A, 802B, 802C is configured to accept a respective plug 803A, 803B, 803C inserted in a joint space JS between the first bone B1 and the second bone B2. When a plug 803A, 803B, 803C is inserted in each of the plug openings 802A, 802B, 802C, the inserted plugs 803A, 803B, 803C are positioned in the joint space JS and can cause compression distraction of the two bones B1, B2. It should thus be appreciated that the orthopaedic implant system of FIG. 8 may be utilized in fusion surgeries where a large joint space is involved to provide sufficient and even compression across the joint space. Alternatively, one or more of the plug openings 802A, 802B, 802C may be configured to accept a respective plug 803A, 803B, 803C inserted in a joint space between, for example the second bone B2 and a third bone, so the orthopaedic implant 800 fuses together three (or more) bones rather than two bones as illustrated.

Figure 9:
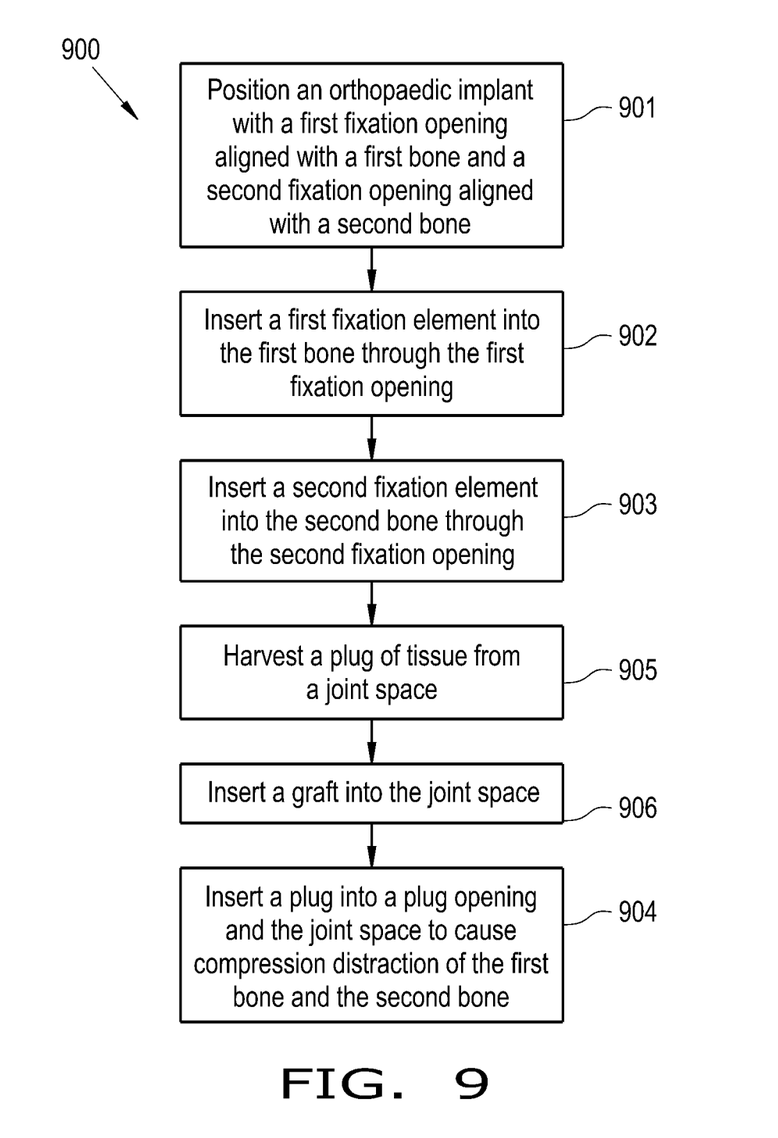
FIG. 9 is a flow chart illustrating an exemplary embodiment of a method of implanting an orthopaedic implant according to the present invention.

Referring now to FIG. 9, an exemplary embodiment of a method 900 of implanting an orthopaedic implant 100, 510, 700, 800 provided according to the present invention is illustrated. The method 900 includes positioning 901 the orthopaedic implant 100, 510, 700, 800 so at least one first fixation opening 101, 511A, 701, 801A is aligned with a first bone B1 and at least one second fixation opening 101, 511B, 701, 801B is aligned with a second bone B2. The method 900 further includes inserting 902 a first fixation element into the first bone B1 through the at least one first fixation opening 101, 511A, 701, 801A and inserting 903 a second fixation element into the second bone B2 through the at least one second fixation opening 101, 511B, 701, 801B. A plug opening 102, 512, 702, 802A, 802B, 802C of the orthopaedic implant 100, 510, 700, 800 is aligned with a joint space JS between the first bone B1 and the second bone B2 after inserting 902 the first fixation element into the first bone B1 and after inserting 903 the second fixation element into the second bone B2. Inserting 902, 903 the fixation elements may be performed after the plug opening 102, 512, 702, 802A, 802B, 802C is already aligned with the joint space JS, with the inserted fixation elements providing initial fixation to maintain the alignment. The plug opening 102, 512, 702, 802A, 802B, 802C defines a plug opening diameter POD that is greater than a diameter FOD of any of the fixation openings 101, 511A, 511B, 701, 801A, 801B and is configured to accept a plug 200, 520, 600, 803A, 803B, 803C inserted in the joint space JS to cause compression distraction of the first bone B1 and the second bone B2. The method 900 may further include inserting 904 a plug 200, 520, 600, 803A, 803B, 803C into the plug opening 102, 512, 702, 802A, 802B, 802C to cause compression distraction of the first bone B1 and the second bone B2, as previously described. In some embodiments, the method 900 also includes harvesting 905 a plug of tissue from the joint space and inserting 906 a graft 530 into the joint space JS after harvesting 905 the plug of tissue. Harvesting 905 the plug of tissue and inserting 906 the graft 530 may both be performed before inserting the plug 200, 520, 600, 803A, 803B, 803C into the plug opening 102, 512, 702, 802A, 802B, 802C. In some embodiments, the plug of tissue is harvested 905 from the joint space JS and/or the graft 530 is inserted into the joint space JS through the plug opening 102, 512, 702, 802A, 802B, 802C without the plug 200, 520, 600, 803A, 803B, 803C inserted therein.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant system, comprising:
   an orthopaedic implant comprising:
      a first fixation opening through a first portion of the orthopaedic implant;
      a second fixation opening through a second portion of the orthopaedic implant; and
      a plug opening through the orthopaedic implant, the plug opening being positioned between the first fixation opening and the second fixation opening;
   wherein:
      a diameter of the plug opening is greater than a diameter of the first fixation opening;
      the diameter of the plug opening is greater than a diameter of the second fixation opening;
      the first fixation opening is configured to receive a first fixation element that is configured to be inserted into a first bone;

the second fixation opening is configured to receive a second fixation element that is configured to be inserted into a second bone;

the plug opening is configured to accept a plug that is configured to be inserted into a joint space between the first bone and the second bone to cause compression distraction of the first bone and the second bone.

2. The orthopaedic implant system of claim 1, further comprising a plug disposed in the plug opening, the plug being configured to cause compression distraction of the first bone and the second bone when inserted in the joint space and disposed in the plug opening.

3. The orthopaedic implant system of claim 2, wherein the plug comprises a head defining a head diameter that is greater than the plug opening diameter.

4. The orthopaedic implant system of claim 3, wherein the plug comprises a cylindrical section and a tapered section defining a tapered diameter that decreases in a direction from the cylindrical section towards a bottom of the plug.

5. The orthopaedic implant system of claim 4, wherein the tapered diameter is less than the plug opening diameter.

6. The orthopaedic implant system of claim 3, wherein a portion of the plug extends out of the plug opening when the plug is fully inserted in the plug opening so the head of the plug abuts against the orthopaedic implant, the portion of the plug extending out of the plug opening defining a protruding length of 2-4 mm.

7. The orthopaedic implant system of claim 2, wherein the plug comprises a polymer.

8. The orthopaedic implant system of claim 2, further comprising a graft compressed by the plug.

9. The orthopaedic implant system of claim 8, wherein the graft comprises biological tissue.

10. The orthopaedic implant system of claim 1, comprising one or more additional fixation openings aligned along a longitudinal axis of the orthopaedic implant with the first fixation opening and one or more additional fixation openings aligned along a width axis of the orthopaedic implant with the second fixation opening.

11. The orthopaedic implant system of claim 1, wherein the orthopaedic implant comprises a first region including the first fixation opening and a second region including the second fixation opening, the first region being connected to the second region by an offsetting region so the first region is lower than the second region.

12. The orthopaedic implant system of claim 11, wherein the offsetting region creates a step between the first region and the second region, the step being between 2-4 mm.

13. The orthopaedic implant system of claim 1, wherein the orthopaedic implant defines a greatest width and the diameter of the plug opening is greater than 50% of the greatest width.

14. The orthopaedic implant system of claim 1, wherein the diameter of the plug opening is at least double the diameter of any of the fixation openings.

15. The orthopaedic implant system of claim 1, wherein the orthopaedic implant comprises a second plug opening and wherein a diameter of the second plug opening is greater than a diameter of any fixation openings of the orthopaedic implant.

16. The orthopaedic implant system of claim 15, wherein the second plug opening is configured to accept a second plug inserted in a joint space between the first bone and the second bone or between the second bone and a third bone.

17. The orthopaedic implant system of claim 15, wherein the diameter of the second plug opening is the same as the diameter of the plug opening.

18. An orthopaedic implant system, comprising:
an orthopaedic implant comprising:
a first fixation opening through the orthopaedic implant;
a second fixation opening through the orthopaedic implant; and
a plug opening through the orthopaedic implant;
a plug configured to be advanced into the plug opening;
wherein:
a diameter of the plug opening is greater than a diameter of the first fixation opening;
the diameter of the plug opening is greater than a diameter of the second fixation opening;
the first fixation opening is configured to receive a first fixation element that is configured to be advanced through the first fixation opening and into bone; and
the second fixation opening is configured to receive a second fixation element that is configured to be advanced through the second fixation opening and into bone;
the plug opening is positioned between the first fixation opening and the second fixation opening and is configured to receive the plug therein;
the orthopaedic system is configured such that, in an operable state with the plug fully inserted into and engaged with the plug opening, the plug extends beyond a bottom surface of the orthopaedic implant by a length of 1-7 mm.

19. The orthopaedic implant system of claim 18, wherein the plug is configured to cause compression distraction of a first bone and a second bone when the plug is inserted into a joint space between the first bone and the second bone and disposed in the plug opening.

20. The orthopaedic implant system of claim 18, wherein the plug comprises one or more threads on an outside surface thereof and the plug opening comprises one or more threads on an inside surface thereof configured to engage with the one or more threads of the plug.

21. The orthopaedic implant system of claim 18, wherein the orthopaedic system is configured such that, in the operable state with the plug fully inserted into and engaged with the plug opening, the plug extends beyond the bottom surface of the orthopaedic implant by a length of 2-4 mm.

22. An orthopaedic implant system, comprising:
an orthopaedic implant comprising:
a first fixation opening through a first portion of the orthopaedic implant;
a second fixation opening through a second portion of the orthopaedic implant; and
a plug opening through the orthopaedic implant; and
a step configured such that a bottom surface of the first portion of the orthopaedic implant is offset from a bottom surface of the second portion of the orthopaedic implant;
a plug configured to be advanced into the plug opening;
wherein:
a diameter of the plug opening is greater than a diameter of the first fixation opening;
the diameter of the plug opening is greater than a diameter of the second fixation opening;
the first fixation opening is configured to receive a first fixation element that is configured to be advanced through the first fixation opening in an operable state of the orthopaedic implant system; and the second fixation opening is configured to receive a second fixation element that is configured to be advanced through the second fixation opening in an operable state of the orthopaedic implant system.

23. The orthopaedic implant system of claim 22, wherein the step is positioned between the first portion of the orthopaedic implant and the second portion of the orthopaedic implant.

\* \* \* \* \*